(12) United States Patent
Kwak et al.

(10) Patent No.: US 10,444,171 B2
(45) Date of Patent: *Oct. 15, 2019

(54) ABSOLUTE POROSITY AND PORE SIZE DETERMINATION OF PORE TYPES IN MEDIA WITH VARYING PORE SIZES

(71) Applicant: Saudi Arabian Oil Company, Dhahran (SA)

(72) Inventors: Hyung T. Kwak, Dhahran (SA); Ali A. Al-Yousif, Dhahran (SA); Salah H. Al-Saleh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/277,470

(22) Filed: Feb. 15, 2019

(65) Prior Publication Data

US 2019/0178825 A1 Jun. 13, 2019

Related U.S. Application Data

(63) Continuation of application No. 15/913,171, filed on Mar. 6, 2018, now Pat. No. 10,288,571.

(60) Provisional application No. 62/468,176, filed on Mar. 7, 2017.

(51) Int. Cl.
| | |
|---|---|
| *G01V 3/00* | (2006.01) |
| *G01N 24/08* | (2006.01) |
| *G01R 33/44* | (2006.01) |
| *G01R 33/46* | (2006.01) |
| *G01N 15/08* | (2006.01) |

(52) U.S. Cl.
CPC ......... *G01N 24/081* (2013.01); *G01N 15/088* (2013.01); *G01N 15/0893* (2013.01); *G01R 33/445* (2013.01); *G01R 33/448* (2013.01); *G01R 33/46* (2013.01); *G01R 33/4641* (2013.01); *Y02A 90/344* (2018.01)

(58) Field of Classification Search
CPC ...................................................... G01N 24/08
USPC ................................................. 324/303, 306
See application file for complete search history.

(56) References Cited

U.S. PATENT DOCUMENTS

| | | | |
|---|---|---|---|
| 9,459,370 B2 | 10/2016 | Korb et al. | |
| 9,625,601 B2 | 4/2017 | Liu et al. | |
| 10,288,571 B2 * | 5/2019 | Kwak | G01R 33/46 |
| 2011/0181277 A1 | 7/2011 | Korb et al. | |

(Continued)

OTHER PUBLICATIONS

International Search Report and Written Opinion dated Jun. 1, 2018 for corresponding PCT/US2018/020650.

(Continued)

*Primary Examiner* — Louis M Arana
(74) *Attorney, Agent, or Firm* — Bracewell LLP; Constance G. Rhebergen; Albert B. Kimball, Jr.

(57) ABSTRACT

The longitudinal relaxation times ($T_1$) of water and hydrocarbon inside porous media, such as rock from subsurface formations, behave differently when external magnetic fields vary. A Nuclear Magnetic Relaxation Dispersion (NMRD) profile from Fast Field Cycling Nuclear Magnetic Resonance (FFC-NMR) technique differentiates the type of fluids filling the pores. Different types of pores in a rock sample are filled with different fluids, water and hydrocarbon, and the absolute porosity and the pore size of each type of pores is determined.

3 Claims, 4 Drawing Sheets

(56) References Cited

U.S. PATENT DOCUMENTS

2017/0115242 A1 4/2017 Kwak et al.
2018/0259466 A1 9/2018 Mitchell et al.
2018/0347351 A1 12/2018 Chen et al.

OTHER PUBLICATIONS

Fleury, Marc: "NMR Relaxation and Petrophysical Properties", AIP Conference Proceedings, Sep. 12, 2011 (Sep. 12, 2011), pp. 9-12, New York, US.
Korb et al., "Dynamical surface affinity of diphasic liquids as a probe of wettability of multimodal porous media", Physical Review E, 2009, pp. 1-12, vol. 80, The American Physical Society.
Korb, et al: "Multi-scales nuclear spin relaxation of liquids in porous media", Comptes Rendus—Physique, Elsevier, Paris FR vol. 11, No. 2, Mar. 1, 2010 (Mar. 1, 2010), pp. 192-203.
Korb, J-P: "Nuclear magnetic relaxation of liquids in porous media;Nuclear magnetic relaxation of liquids in porous media". New Journal of Physics, Institute of Physics Publishing, Bristol, GB, vol. 13, No. 3, Mar. 22, 2011 (Mar. 22, 2011), p. 35016.

\* cited by examiner

ABSOLUTE POROSITY AND PORE SIZE DETERMINATION OF PORE TYPES IN MEDIA WITH VARYING PORE SIZES

This application is a continuation of, and claims priority for the filing date of, commonly owned, co-pending U.S. patent application Ser. No. 15/913,171 filed on Mar. 6, 2018, which in turn claims priority for the filing date of U.S. Provisional Application No. 62/468,176 filed Mar. 7, 2017. For purposes of United States patent practice, this application incorporates the contents of the Provisional Application by reference in entirety.

BACKGROUND OF THE INVENTION

1. Field of the Invention

The present invention relates to absolute porosity and pore size determination of pore types with varying pore sizes in porous media from subsurface formations, and more particularly to absolute porosity and pore size determination with a Nuclear Magnetic Relaxation Dispersion (NMRD) profile from a Fast Field Cycling Nuclear Magnetic Resonance (FFC-NMR) measure.

2. Description of the Related Art

Accurate knowledge of formation rock porosity is important. The value of estimating accurate reserves by identifying accurate porosities with movable fluids is very important. In addition, the accurate measurement of actual pore size determination with non-destructive method adds great value for various petrophysical properties measurements.

Accurate measurement of porosity and pore size corresponding to each pore types is important for reservoir characterization. Porous media with various pore sizes are common, such as carbonate rocks encountered in hydrocarbon producing formations of reservoirs. Non-destructive methods for measuring the absolute porosity of each pore types, however, are not available, as far as is known. Since these pores with different sizes are interconnected to each other by diffusion coupling, the measurement of true porosity of each pore type is not a trivial process.

Due to the lack of absolute porosity data for different pore types in reservoir rocks, mostly carbonates, the current reserve estimations methods based on porosity data have suffered from a considerable margin of errors.

Pore throat size distribution can be provided by laboratory mercury injection capillary pressure (MICP) data, but pore throat size is different from pore body size. Porosity measurement by micro-CT (microcomputed tomography) can provide the pore size and absolute porosity of each pore types, but it requires a contrast cutoff value to differentiate between pore and matrix. However, micro-CT is not a physical measurement, but a data estimation process. In addition the sample size of MICP and micro-CT are usually too small to be a representative volume of a formation rock with inhomogeneous pore size distribution.

Pore throat size distribution determination with low-field NMR relaxometry methods has also been attempted. However, the results have been subject to a certain degree of uncertainly due to the data analysis by 1D and 2D inversion processes.

Prior art techniques have been able to distinguish between fluid types (hydrocarbon and water) in rock samples pores by identifying biphasic behavior of water and hydrocarbon, but so far as is known not to identify the absolute porosity and pore size determination of each pore types.

SUMMARY OF THE INVENTION

Briefly, the present invention provides a new and improved method of obtaining a measure of porosity and pore size in a rock sample from a subsurface hydrocarbon reservoir. Nuclear magnetic resonance relaxation times are obtained of the rock sample fully saturated with water, and a nuclear magnetic resonance dispersion profile obtained of the rock sample at irreducible water saturation. The pore types in the pores of the rock sample are then identified based on the obtained nuclear magnetic resonance dispersion profile of the rock sample at irreducible water saturation. Porosity of the identified pore types is determined based on the nuclear magnetic resonance relaxation times, and pore size of the identified pore types is determined based on the nuclear magnetic resonance relaxation times.

The present invention also provides a new and improved method of obtaining a measure of porosity and pore size in a rock sample. Nuclear magnetic resonance relaxation times are obtained of the rock sample fully saturated with water, and a nuclear magnetic resonance dispersion profile obtained of the rock sample at irreducible water saturation. The pore types in the pores of the rock sample are then identified based on the obtained nuclear magnetic resonance dispersion profile of the rock sample at irreducible water saturation. Porosity of the identified pore types is determined based on the nuclear magnetic resonance relaxation times, and pore size of the identified pore types is determined based on the nuclear magnetic resonance relaxation times.

DETAILED DESCRIPTION OF THE PREFERRED EMBODIMENTS

Figure 1:
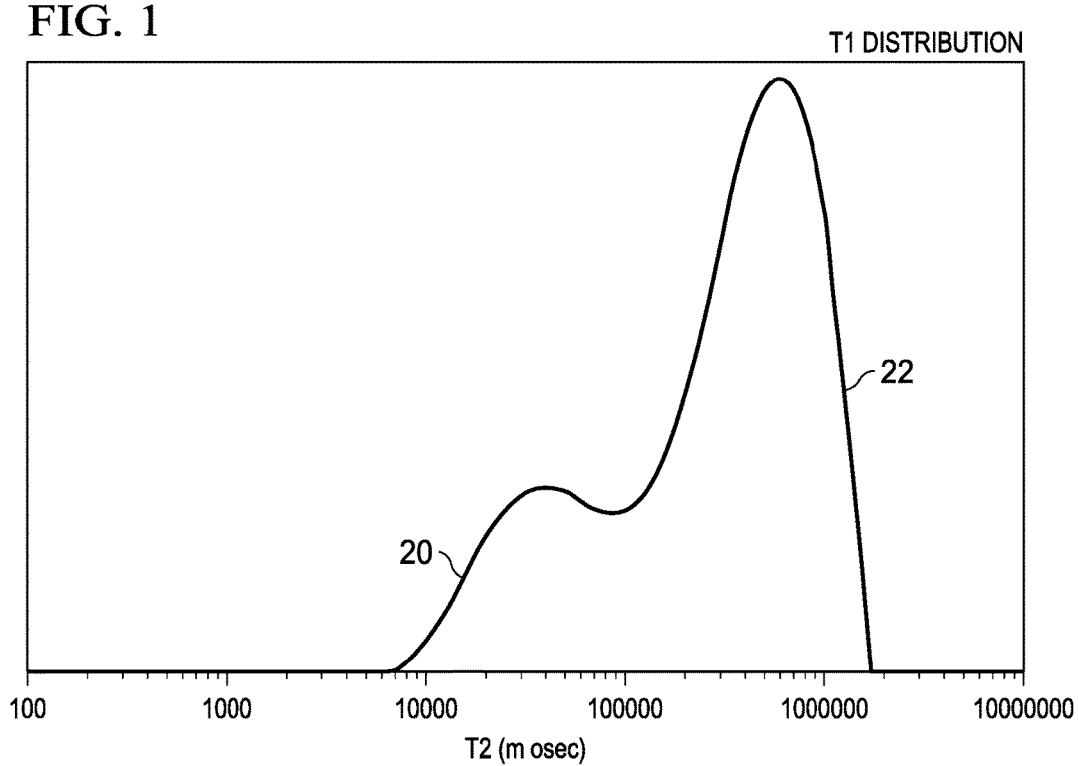
FIG. 1 is an example plot of NMR relaxation distribution time distribution of carbonate rocks with two different pore types or sizes.
Figure 2:
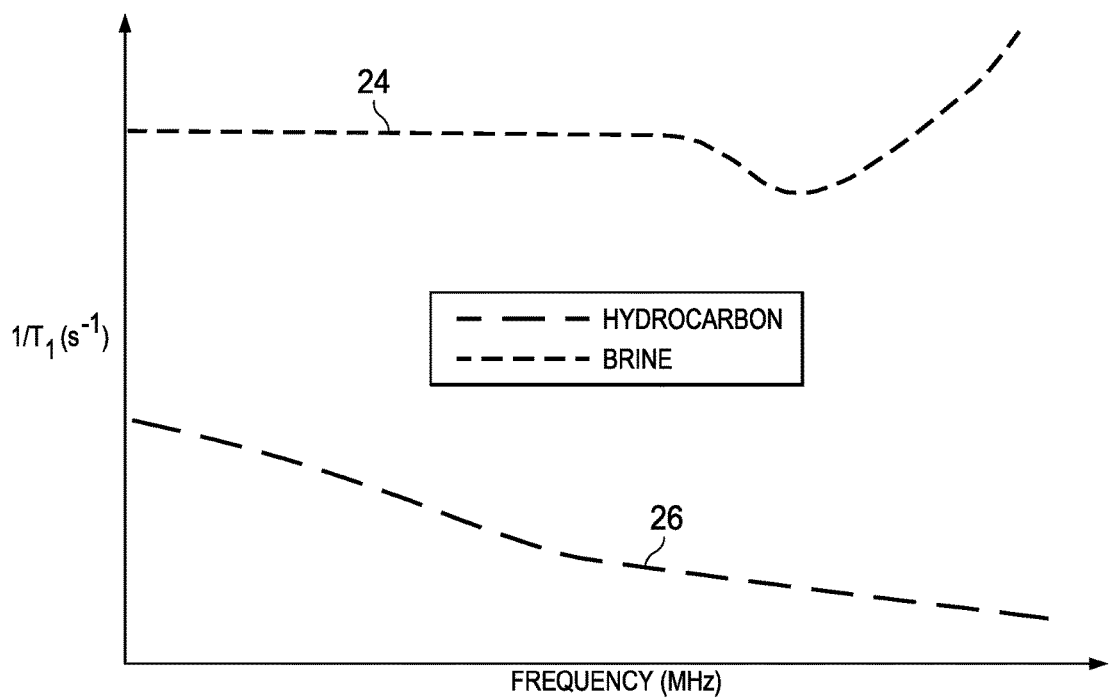
FIG. 2 are example plots of nuclear magnetic relaxation dispersion or NMRD profiles obtained from a rock sample saturated with brine, and with hydrocarbons.

In the drawings, FIG. 1 shows an example of $T_1$ distribution obtained by nuclear magnetic resonance relaxometry of carbonate rocks with two different pore types (sizes), as indicated by overlapping peaks 20 and 22. The overlap of $T_1$ distribution is due to the diffusion coupling between the two different pore sizes or types, thus the absolute porosity of each pore type cannot be extracted from the currently practiced low-field NMR measurement due to the overlapped distributions. FIG. 2 is a composite plot of nuclear magnetic relaxation dispersion or NMRD profiles obtained from a rock sample. The plot 24 is for an example rock sample saturated with brine, while the plot 26 is for an example rock sample saturated with hydrocarbons. The differences between plot 24 and 26 are caused by different fluid-rock interactions between brine and hydrocarbon.

With the present invention, it has been found that an NMRD profile like that of FIG. 2, after careful sample preparation of the rock sample, can result in providing absolute porosity and pore diameter determination for the rock sample. As will be set forth, the process according to the present invention causes the small pores to be fully saturated with brine, and the large pores are saturated only with hydrocarbons. This in turn permits the absolute porosity and pore diameter determination, when surface relaxivity is known for each of the pore types.

The longitudinal relaxation times ($T_1$) of water and hydrocarbon inside porous media, such as rock, behave differently when external magnetic fields vary. Thus, with the present invention, a Nuclear Magnetic Relaxation Dispersion (NMRD) profile obtained with a Fast Field Cycling Nuclear Magnetic Resonance (FFC-NMR) technique can differentiate the type of fluids filled the pores. Thus, if the different types of pores are filled with different fluids, water and hydrocarbon, then, the absolute porosity and the pore size of each type of pores can be measured.

Due to the existence of paramagnetic ions on reservoir rocks, the NMRD profiles of water and hydrocarbon are different in the rock. The present invention uses this clear detectability of water and hydrocarbon in different pores systems to provide absolute porosity and pore size determination of pore types in media with varying pore sizes.

Figure 3:
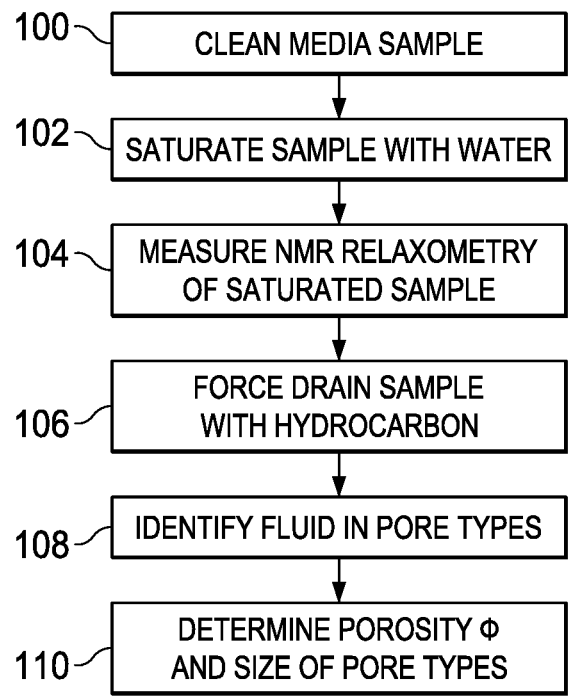
FIG. 3 is a schematic diagram of a process for measuring absolute porosity and pore size between different pore types in porous media according to the present invention.

A comprehensive methodology of absolute porosity and pore size determination of pore types in porous media according to the present invention is illustrated schematically in FIG. 3. As indicated at step 100, the rock sample is fully cleaned in the conventional manner with a series of organic solvents to achieve water-wet porous media. After the cleaning, the work is thus strongly water-wet. Then, during step 102, the rock sample is fully saturated with brine or de-ionized water.

Figure 4:
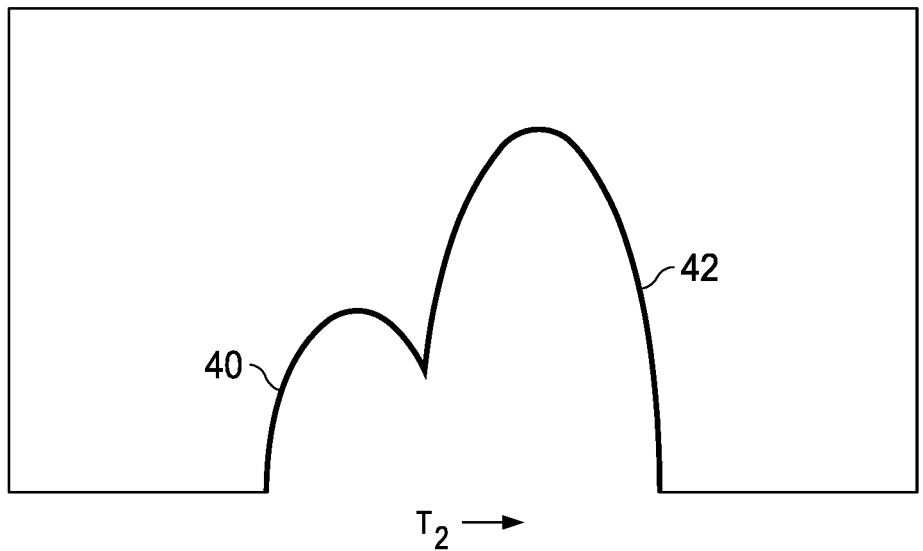
FIG. 4 is an example plot of NMR relaxation distribution time distribution between pores of a rock sample saturated with brine during the process according to FIG. 3.

During step 104, measures of $T_1$ NMR relaxometry are taken of the brine saturated sample with a suitable low-field NMR instrument with external magnetic field usually lower than 1 Tesla to achieve $T_1$ distribution of pores in the sample. FIG. 4 illustrates an example $T_1$ distribution of the cleaned and fully brine saturated rock sample as a result of step 104. An overlapping distribution of peaks 40 and 42 like that of FIG. 2 is present.

Figure 5:
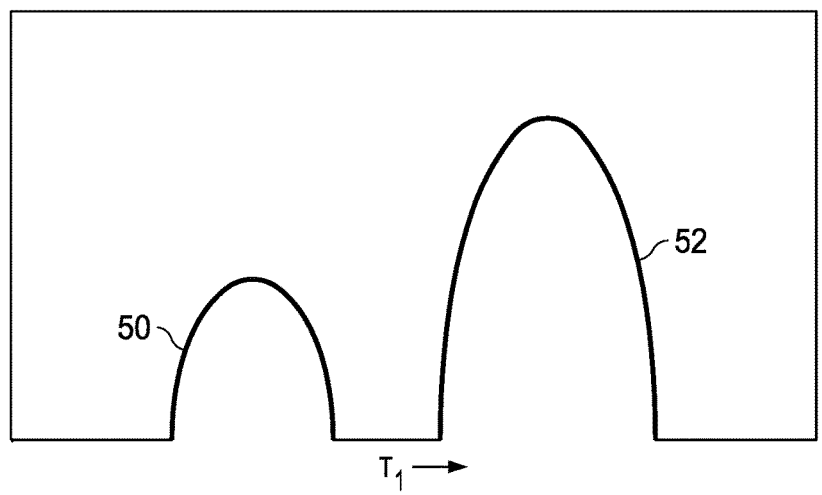
FIG. 5 is an example plot of NMR relaxation distribution time distribution between pores of a rock sample saturated with hydrocarbon at irreducible water saturation during the process according to FIG. 3.

During step 106, forced drainage of the sample is conducted with a hydrocarbon, preferably pure alkane liquids, such as Dodecane, until an irreducible water saturation or $S_{wirr}$ stage is reached. FIG. 5 illustrates an example $T_1$ distribution of the rock sample after forced drainage at $S_{wirr}$ as a result of step 106. As indicated at 50 and 52, the distribution peaks do not overlap for the drained sample. During step 108, an NMRD profile acquisition of the sample is performed by FFC-NMR technique with a Fast Field Cycling NMR instrument. The variation of external magnetic field strength for the NMRD profile measurement preferably ranges from a few kHz up to tens of MHz which is enough to show the different characteristics of brine and hydrocarbon on the pore surface. At irreducible water saturation in the oil zone $S_{wirr}$, small and large pores in the sample are fully saturated with only brine and only hydrocarbon, respectively. The measured NMRD profiles can according to the present invention identify each pore types by accurately detecting the fluid in each pore system.

Figure 6:
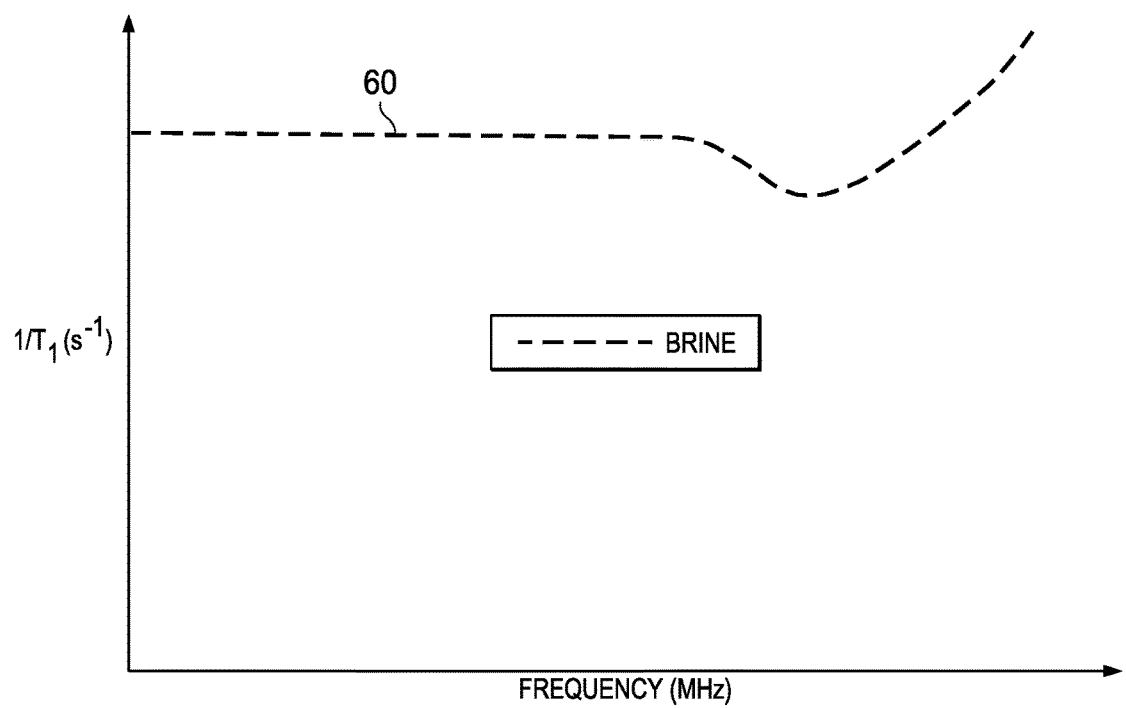
FIG. 6 is an example plot of nuclear magnetic relaxation dispersion or NMRD profiles obtained according to the present invention from a rock sample saturated with brine during the process according to FIG. 3.
Figure 7:
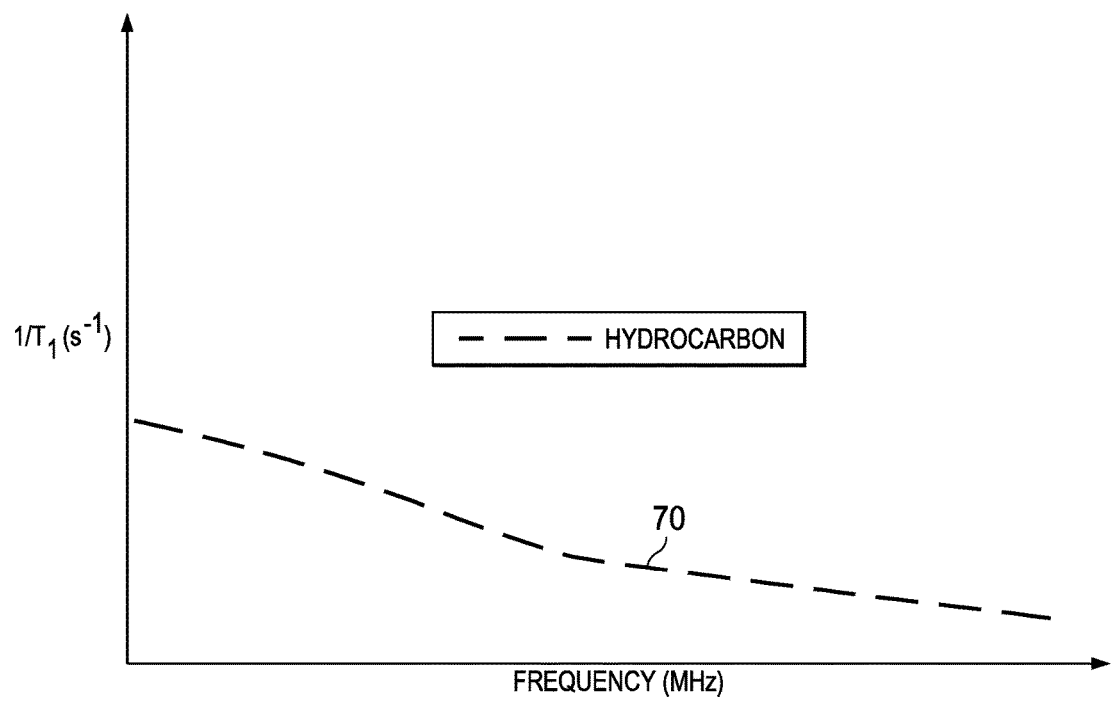
FIG. 7 is an example plot of nuclear magnetic relaxation dispersion or NMRD profiles obtained according to the present invention from a rock sample fully saturated with hydrocarbons during the process according to FIG. 3.
Figure 8:
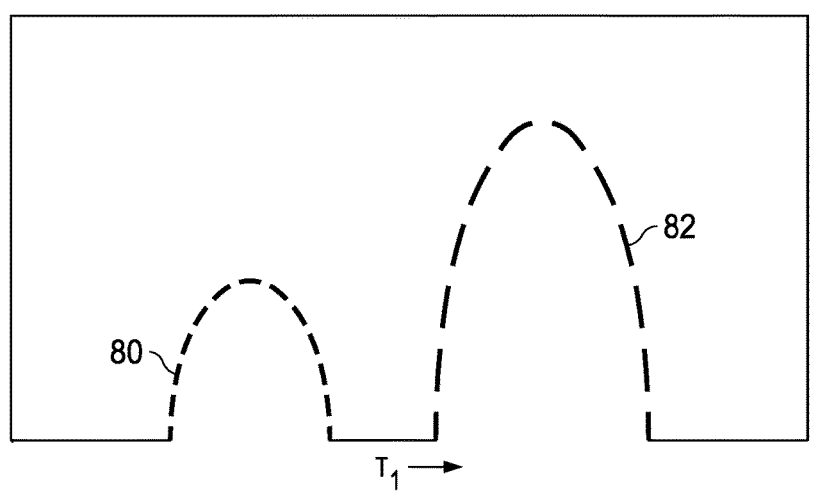
FIG. 8 is an example plot of NMR relaxation distribution time distribution between small pores and large pores of a rock sample obtained during the process according to FIG. 3.

As a result of step 108, the measured NMRD profiles identify each pore types by in each pore system. FIG. 6 illustrates at 60 an example NMRD profile of brine small pores obtained during step 108. FIG. 7 illustrates at 70 a measured NMRD profile of large pores. During step 110, the fluid in each type of pores is identified by analysis of the NMRD profile of each pore, as will be described below. FIG. 8 illustrates at 80 identified $T_1$ distribution of a pore type filled with brine only, and at 82 an identified $T_1$ distribution of a pore type filled with hydrocarbon only.

During step 110, the porosity and pore size of each pore types identified during step as a result of step 108 is determined from $T_1$ distribution of the sample at $S_{wirr}$. The porosity can be easily calculated from the area under each $T_1$ distribution peak for each pore types. The method calculating the pore size of each pore types will be described below. The $T_1$ relaxation time in the porous media can be expressed as Equation (1):

$$\frac{1}{T_1(\omega_I)} = \frac{1}{T_{1,bulk}} + \frac{N_{surface}}{N} \frac{1}{T_{1,2D}(\omega_I)} + \frac{N_{param}}{N} \frac{1}{T_{1,param}(\omega_I)} \quad (1)$$

where $T_{1,bulk}$ is the $T_1$ relaxation time of bulk fluid, $N_{surface}/N$ is the ratio between the number of liquid molecules diffusion within the thin transient layer close to the pore surface and in the bulk, $T_{1,2D(\omega_I)}$ is $T_1$ relaxation time due to 2D diffusional motion on the surface, $N_{param}/N$ is the ratio between the number of liquid molecules bonded to the paramagnetic sites at the surface and in the bulk, and $T_{1,param}$ is the $T_1$ relaxation time dominated by the interaction of proton with paramagnetic ions on the surface.

The $T_1$ relaxation time of brine and hydrocarbon is dominated by $T_{1,param}$ and $T_{1,2D}$, respectively (Equations 2 and 3). Thus, this biphasic behavior of brine and hydrocarbon in the porous media is utilized to identify the type of fluids in the specific pores in the porous media of interests.

$$\frac{1}{T_{1,protic}(\omega_I)} = \frac{1}{T_{1,brine}(\omega_I)} = \frac{1}{T_{1,bulk}} + \frac{N_{param}}{N} \frac{1}{T_{1,param}(\omega_I)} = \quad (2)$$
$$\frac{1}{T_{1,bulk}} + \rho_{1,s}\left(\frac{S}{V}\right) \cong \frac{1}{T_{1,bulk}} + \rho_{1,s}\left(\frac{1}{r_s}\right)$$

$$\frac{1}{T_{1,aprotic}(\omega_I)} = \frac{1}{T_{1,hydrocarbon}(\omega_I)} = \quad (3)$$
$$\frac{1}{T_{1,bulk}} + \frac{N_{surface}}{N} \frac{1}{T_{1,2D}(\omega_I)} = \frac{1}{T_{1,bulk}} + \left(\frac{S}{V}\right) \cong \frac{1}{T_{1,bulk}} \rho_{1,l}\left(\frac{1}{r_l}\right)$$

where $\rho_{1,s}$ and $\rho_{1,l}$ is the surface relaxivity of $T_1$ for small and large pores, respectively. The last approximation steps of both equations (2) and (3) are based on the assumption that the shape of pores is spherical which is satisfactorily adequate. The value $r_s$ and $r_l$ represent the radius of small and large pores, respectively.

In the case the amount of paramagnetic ion on the surface of porous media is not enough to produce the diphasic NMRD profile from brine and hydrocarbon, it has to be treated with a certain amount of paramagnetic ions before the workflow of the process of FIG. 3. The result of the treatment with paramagnetic can be confirmed by the comparison of $T_1$ NMR distribution before and after the treatment. Once injected paramagnetic ions coated all pores, then $T_2$ distribution of all pore types shift toward shorter time.

The present invention thus provides a new method to measure absolute porosity and pore size value from porous media with various pore sizes non-destructively by Nuclear Magnetic Relaxation Dispersion (NMRD) profile techniques. Accurate measurement of absolute porosity and pore size of each pore type with the present invention greatly improves the accuracy of these reserve estimation based on porosity data from reservoirs.

The invention has been sufficiently described so that a person with average knowledge in the matter may reproduce and obtain the results mentioned in the invention herein Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. A method of obtaining a measure of porosity and pore size in the rock sample from a subsurface hydrocarbon reservoir from nuclear magnetic resonance dispersion profiles of the rock sample and nuclear magnetic resonance relaxation times, comprising the steps of:
    treating the rock sample with paramagnetic ions to coat pores on the rock sample to produce the nuclear magnetic resonance dispersion profiles;
    obtaining nuclear magnetic resonance relaxation times of the rock sample fully saturated with water;
    obtaining a nuclear magnetic resonance dispersion profile of the rock sample at irreducible water saturation;
    identifying pore types in the pores of the rock sample based on the obtained nuclear magnetic resonance dispersion profile of the rock sample at irreducible water saturation;
    determining porosity of the identified pore types based on the nuclear magnetic resonance relaxation times; and
    determining pore size of the identified pore types based on the nuclear magnetic resonance relaxation times.

2. A method of obtaining a measure of absolute porosity and pore size of pore types in a rock sample from nuclear magnetic resonance dispersion profiles of the rock sample and nuclear magnetic resonance relaxation times, comprising the steps of:
    treating the rock sample with paramagnetic ions to coat pores on the rock sample to produce the nuclear magnetic resonance dispersion profiles;
    obtaining nuclear magnetic resonance relaxation times of the rock sample fully saturated with water;
    obtaining a nuclear magnetic resonance dispersion profile of the rock sample at irreducible water saturation;
    identifying pore types in the pores of the rock sample based on the obtained nuclear magnetic resonance dispersion profile of the rock sample at irreducible water saturation;
    determining absolute porosity of the identified pore types based on the nuclear magnetic resonance relaxation times; and
    determining pore size of the identified pore types based on the nuclear magnetic resonance relaxation times.

3. A method of obtaining a measure of porosity and pore size in the rock sample from a subsurface hydrocarbon reservoir, comprising the steps of:
    obtaining nuclear magnetic resonance relaxation times of the rock sample fully saturated with water;
    conducting forced drainage of the rock sample by fully saturating the rock sample with hydrocarbon liquid to obtain irreducible water saturation of the rock sample;
    obtaining a nuclear magnetic resonance dispersion profile of the rock sample at irreducible water saturation;
    identifying pore types in the pores of the rock sample based on the obtained nuclear magnetic resonance dispersion profile of the rock sample at irreducible water saturation;
    determining porosity of the identified pore types based on the nuclear magnetic resonance relaxation times; and
    determining pore size of the identified pore types based on the nuclear magnetic resonance relaxation times.

* * * * *